United States Patent
Howell et al.

(10) Patent No.: US 11,648,377 B2
(45) Date of Patent: May 16, 2023

(54) CATHETER SECUREMENT DEVICE INCLUDING A GUIDING NOSE

(71) Applicant: C. R. Bard, Inc., Murray Hill, NJ (US)

(72) Inventors: Glade H. Howell, Draper, UT (US); Jeremy A. Pearce, West Jordan, UT (US); Ruben Ramirez, Sandy, UT (US)

(73) Assignee: C. R. Bard, Inc., Franklin Lakes, NJ (US)

( * ) Notice: Subject to any disclaimer, the term of this patent is extended or adjusted under 35 U.S.C. 154(b) by 181 days.

(21) Appl. No.: 15/594,507

(22) Filed: May 12, 2017

(65) Prior Publication Data
US 2017/0326340 A1    Nov. 16, 2017

Related U.S. Application Data

(60) Provisional application No. 62/336,496, filed on May 13, 2016.

(51) Int. Cl.
*A61M 25/02* (2006.01)
*A61F 13/00* (2006.01)
*A61M 25/00* (2006.01)

(52) U.S. Cl.
CPC ....... *A61M 25/02* (2013.01); *A61F 13/00034* (2013.01); *A61M 2025/0098* (2013.01);
(Continued)

(58) Field of Classification Search
CPC .......... A61M 25/02; A61M 2025/0213; A61M 2025/024; A61M 2025/0246;
(Continued)

(56) References Cited

U.S. PATENT DOCUMENTS

| | | |
|---|---|---|
| 1,850,362 A | 3/1932 | Vogel |
| 3,589,361 A | 6/1971 | Loper et al. |

(Continued)

FOREIGN PATENT DOCUMENTS

| | | |
|---|---|---|
| WO | 9219309 A1 | 11/1992 |
| WO | 9421319 A1 | 9/1994 |

(Continued)

OTHER PUBLICATIONS

PCT/US2017/032558 filed May 12, 2017 International Search Report and Written Opinion dated Aug. 3, 2017.
(Continued)

*Primary Examiner* — Kami A Bosworth
(74) *Attorney, Agent, or Firm* — Rutan & Tucker LLP (57) ABSTRACT

A securement device configured to secure an external portion of a medical device to the skin surface of a patient after an internal portion of the device has been placed in the patient is disclosed. The securement device includes a retainer that is employed to securely retain the external portion of the medical device in place. The retainer is attached to a base, such as an adhesive pad that adhesively attaches to the skin surface. In one embodiment, therefore, a retainer comprises a body defining a channel configured to receive therein a portion of the medical device, and at least one foot extending from the body that is configured to stabilize the retainer with respect to a skin surface. The retainer body further includes a nose that is configured to deflect a portion of the external portion of the medical device toward the skin insertion site.

34 Claims, 9 Drawing Sheets

(52) U.S. Cl.
CPC . *A61M 2025/024* (2013.01); *A61M 2025/028* (2013.01); *A61M 2025/0246* (2013.01); *A61M 2025/0266* (2013.01)

(58) Field of Classification Search
CPC .... A61M 2025/0253; A61M 2025/026; A61M 2025/0266; A61M 2025/0273; A61M 2025/028; A61M 2025/0286; A61M 2025/0098
See application file for complete search history.

(56) References Cited

U.S. PATENT DOCUMENTS

| | | | |
|---|---|---|---|
| 3,605,725 A | 9/1971 | Bentov | |
| 3,900,026 A * | 8/1975 | Wagner | A61M 25/02 128/888 |
| 3,901,226 A * | 8/1975 | Scardenzan | A61M 5/00 128/888 |
| 3,921,631 A | 11/1975 | Thompson | |
| 3,973,565 A | 8/1976 | Steer | |
| 4,161,177 A | 7/1979 | Fuchs | |
| 4,224,937 A | 9/1980 | Gordon | |
| 4,250,880 A | 2/1981 | Gordon | |
| 4,362,156 A | 12/1982 | Feller, Jr. et al. | |
| 4,397,641 A | 8/1983 | Jacobs | |
| 4,435,174 A | 3/1984 | Redmond et al. | |
| 4,457,754 A | 7/1984 | Buttaravoli | |
| 4,490,141 A | 12/1984 | Lacko et al. | |
| 4,534,762 A * | 8/1985 | Heyer | A61M 25/02 128/DIG. 26 |
| 4,579,120 A | 4/1986 | MacGregor | |
| 4,614,183 A | 9/1986 | McCracken et al. | |
| 4,645,492 A | 2/1987 | Weeks | |
| 4,711,636 A | 12/1987 | Bierman | |
| 4,743,232 A | 5/1988 | Kruger | |
| 4,834,712 A | 5/1989 | Quinn et al. | |
| 4,838,868 A | 6/1989 | Forgar et al. | |
| 4,915,694 A | 4/1990 | Yamamoto et al. | |
| 4,976,700 A | 12/1990 | Tollini | |
| 5,192,273 A | 3/1993 | Bierman | |
| 5,192,274 A | 3/1993 | Bierman | |
| 5,267,968 A | 12/1993 | Russo | |
| 5,290,248 A | 3/1994 | Bierman et al. | |
| 5,314,411 A | 5/1994 | Bierman et al. | |
| 5,318,546 A | 6/1994 | Bierman | |
| 5,330,461 A | 7/1994 | Leeker | |
| 5,354,282 A | 10/1994 | Bierman | |
| 5,395,344 A | 3/1995 | Beisang, III et al. | |
| 5,413,562 A * | 5/1995 | Swauger | A61M 25/02 128/DIG. 26 |
| 5,456,671 A | 10/1995 | Bierman | |
| 5,484,420 A | 1/1996 | Russo | |
| 5,554,106 A | 9/1996 | Layman-Spillar et al. | |
| D375,355 S | 11/1996 | Bierman | |
| D375,356 S | 11/1996 | Bierman | |
| 5,578,013 A | 11/1996 | Bierman | |
| 5,626,565 A | 5/1997 | Landis et al. | |
| 5,637,098 A | 6/1997 | Bierman | |
| 5,686,096 A | 11/1997 | Khan et al. | |
| 5,693,032 A | 12/1997 | Bierman | |
| 5,702,371 A | 12/1997 | Bierman | |
| 5,722,959 A | 3/1998 | Bierman | |
| 5,800,402 A | 9/1998 | Bierman | |
| 5,810,781 A | 9/1998 | Bierman | |
| 5,827,230 A | 10/1998 | Bierman | |
| 5,833,663 A | 11/1998 | Bierman et al. | |
| 5,833,665 A | 11/1998 | Bootman et al. | |
| 5,833,667 A | 11/1998 | Bierman | |
| D404,815 S | 1/1999 | Bierman | |
| 5,855,591 A | 1/1999 | Bierman | |
| 5,941,263 A | 8/1999 | Bierman | |
| 5,947,931 A | 9/1999 | Bierman | |
| D425,619 S | 5/2000 | Bierman | |
| 6,117,163 A | 9/2000 | Bierman | |
| 6,132,398 A | 10/2000 | Bierman | |
| 6,213,979 B1 | 4/2001 | Bierman | |
| 6,224,571 B1 | 5/2001 | Bierman | |
| 6,273,873 B1 | 8/2001 | Fleischer | |
| 6,283,945 B1 | 9/2001 | Bierman | |
| 6,290,676 B1 | 9/2001 | Bierman | |
| 6,302,867 B1 | 10/2001 | Brown, Jr. et al. | |
| 6,361,523 B1 | 3/2002 | Bierman | |
| 6,413,240 B1 | 7/2002 | Bierman et al. | |
| 6,428,515 B1 | 8/2002 | Bierman et al. | |
| 6,428,516 B1 | 8/2002 | Bierman | |
| 6,436,073 B1 | 8/2002 | Von Teichert | |
| 6,447,485 B2 | 9/2002 | Bierman | |
| 6,482,183 B1 | 11/2002 | Pausch et al. | |
| 6,491,664 B2 | 12/2002 | Bierman | |
| D470,936 S | 2/2003 | Bierman | |
| 6,551,284 B1 | 4/2003 | Greenberg et al. | |
| 6,551,285 B1 | 4/2003 | Bierman | |
| 6,572,588 B1 | 6/2003 | Bierman et al. | |
| 6,582,403 B1 | 6/2003 | Bierman et al. | |
| 6,663,600 B2 | 12/2003 | Bierman et al. | |
| 6,673,046 B2 | 1/2004 | Bierman et al. | |
| 6,689,104 B2 | 2/2004 | Bierman | |
| D492,411 S | 6/2004 | Bierman | |
| 6,770,055 B2 | 8/2004 | Bierman et al. | |
| 6,786,892 B2 | 9/2004 | Bierman | |
| 6,796,310 B2 | 9/2004 | Bierman | |
| 6,827,705 B2 | 12/2004 | Bierman | |
| 6,827,706 B2 | 12/2004 | Tollini | |
| 6,827,707 B2 | 12/2004 | Wright et al. | |
| 6,837,875 B1 | 1/2005 | Bierman | |
| 6,866,652 B2 | 3/2005 | Bierman | |
| D503,977 S | 4/2005 | Bierman | |
| 6,929,625 B2 | 8/2005 | Bierman | |
| 6,948,500 B2 | 9/2005 | Bierman | |
| 6,951,550 B2 | 10/2005 | Bierman | |
| 6,972,003 B2 | 12/2005 | Bierman et al. | |
| 6,979,320 B2 | 12/2005 | Bierman | |
| 7,014,627 B2 | 3/2006 | Bierman | |
| 7,018,362 B2 | 3/2006 | Bierman et al. | |
| 7,025,749 B2 | 4/2006 | Propp | |
| 7,094,944 B2 | 8/2006 | Faasse, Jr. | |
| D528,206 S | 9/2006 | Bierman | |
| 7,147,620 B2 | 12/2006 | Kessler et al. | |
| 7,153,291 B2 | 12/2006 | Bierman | |
| 7,204,827 B2 | 4/2007 | Kessler | |
| 7,223,256 B2 | 5/2007 | Bierman | |
| D547,862 S | 7/2007 | Dikeman et al. | |
| 7,247,150 B2 | 7/2007 | Bierman | |
| D552,732 S | 10/2007 | Bierman et al. | |
| 7,316,679 B2 | 1/2008 | Bierman | |
| 7,317,134 B2 | 1/2008 | Faasse, Jr. | |
| D563,552 S | 3/2008 | Bierman et al. | |
| D567,941 S | 4/2008 | Dikeman et al. | |
| 7,354,421 B2 | 4/2008 | Bierman | |
| D568,466 S | 5/2008 | Dikeman et al. | |
| D569,506 S | 5/2008 | Dikeman et al. | |
| D577,437 S | 9/2008 | Bierman et al. | |
| 7,491,190 B2 | 2/2009 | Bierman et al. | |
| 7,520,870 B2 | 4/2009 | Bierman | |
| 7,563,251 B2 | 7/2009 | Bierman et al. | |
| 7,568,484 B2 | 8/2009 | Bierman et al. | |
| 7,578,804 B2 | 8/2009 | Bierman | |
| 7,591,803 B2 | 9/2009 | Bierman | |
| 7,611,493 B2 | 11/2009 | Jonsson | |
| 7,626,070 B2 | 12/2009 | Propp | |
| 7,628,154 B2 | 12/2009 | Bierman et al. | |
| 7,628,771 B2 | 12/2009 | Kessler | |
| 7,635,355 B2 | 12/2009 | Bierman | |
| 7,648,492 B2 | 1/2010 | Bierman | |
| 7,651,479 B2 | 1/2010 | Bierman | |
| 7,660,615 B2 | 2/2010 | VanAntwerp et al. | |
| 7,666,167 B2 | 2/2010 | Bierman | |
| D613,857 S | 4/2010 | Bierman | |
| D613,858 S | 4/2010 | Bierman | |
| D613,859 S | 4/2010 | Bierman | |
| D613,860 S | 4/2010 | Bierman et al. | |
| 7,690,608 B2 | 4/2010 | Huber | |
| 7,691,096 B2 | 4/2010 | Gillis | |

(56) References Cited

U.S. PATENT DOCUMENTS

| | | |
|---|---|---|
| 7,722,571 B2 | 5/2010 | Bierman et al. |
| 7,723,561 B2 | 5/2010 | Propp |
| D618,792 S | 6/2010 | Bierman |
| 7,744,572 B2 | 6/2010 | Bierman |
| 7,758,586 B2 | 7/2010 | Muto et al. |
| 7,762,991 B2 | 7/2010 | Bierman et al. |
| D622,841 S | 8/2010 | Bierman |
| 7,780,634 B2 | 8/2010 | Propp |
| 7,785,295 B2 | 8/2010 | Bierman |
| 7,799,001 B2 | 9/2010 | Bierman |
| 7,806,873 B2 | 10/2010 | Dikeman et al. |
| 7,811,258 B2 | 10/2010 | Bierman |
| 7,837,655 B2 | 11/2010 | Bierman et al. |
| D629,512 S | 12/2010 | Bierman et al. |
| D629,513 S | 12/2010 | Bierman et al. |
| D629,514 S | 12/2010 | Bierman |
| 7,879,013 B2 | 2/2011 | Smith et al. |
| 7,887,515 B2 | 2/2011 | Bierman |
| 7,935,083 B2 | 5/2011 | Bierman et al. |
| 7,935,084 B2 | 5/2011 | Bierman |
| 7,955,307 B2 | 6/2011 | Bierman et al. |
| 7,967,792 B2 | 6/2011 | Bierman |
| 7,972,310 B2 | 7/2011 | Kessler |
| 7,981,087 B2 | 7/2011 | Gesler, III |
| 7,985,205 B2 | 7/2011 | Adams |
| 7,985,206 B2 | 7/2011 | Dikeman et al. |
| 7,988,673 B2 | 8/2011 | Wright et al. |
| 8,016,792 B2 | 9/2011 | Wright et al. |
| 8,016,793 B2 | 9/2011 | Wright et al. |
| 8,025,060 B2 | 9/2011 | Bierman |
| 8,025,643 B2 | 9/2011 | Bierman |
| 8,043,280 B2 | 10/2011 | Bierman |
| 8,052,648 B2 | 11/2011 | Dikeman et al. |
| 8,052,649 B2 | 11/2011 | Wright |
| 8,052,652 B2 | 11/2011 | Bierman et al. |
| 8,053,623 B2 | 11/2011 | Propp |
| 8,057,440 B2 | 11/2011 | Bierman |
| 8,074,651 B2 | 12/2011 | Bierman et al. |
| 8,100,862 B2 | 1/2012 | Bierman |
| 8,105,289 B2 | 1/2012 | Bierman et al. |
| 8,105,290 B2 | 1/2012 | Wright et al. |
| 8,114,054 B2 | 2/2012 | Bierman et al. |
| 8,128,602 B2 | 3/2012 | Tollini et al. |
| 8,146,210 B2 | 4/2012 | Nishtala |
| 8,157,770 B2 | 4/2012 | Elwell et al. |
| 8,162,898 B1 | 4/2012 | Wright |
| 8,172,807 B2 | 5/2012 | Dikeman et al. |
| 8,177,756 B2 | 5/2012 | Wright |
| 8,197,447 B2 | 6/2012 | Wright |
| 8,211,063 B2 | 7/2012 | Bierman et al. |
| 8,211,064 B2 | 7/2012 | Sloan |
| 8,212,101 B2 | 7/2012 | Propp |
| 8,241,253 B2 | 8/2012 | Bracken |
| 8,246,583 B2 | 8/2012 | Bierman |
| 8,251,956 B2 | 8/2012 | Bierman et al. |
| 8,269,059 B2 | 9/2012 | Wright et al. |
| 8,277,420 B2 | 10/2012 | Bierman et al. |
| 8,282,606 B2 | 10/2012 | Bierman |
| 8,298,191 B2 | 10/2012 | Bierman et al. |
| 8,333,736 B2 | 12/2012 | Wright et al. |
| 8,353,876 B2 | 1/2013 | Suwito et al. |
| 8,357,124 B2 | 1/2013 | Bierman |
| 8,366,678 B2 | 2/2013 | Bierman et al. |
| 8,394,065 B2 | 3/2013 | Bierman |
| 8,394,067 B2 | 3/2013 | Bracken et al. |
| 8,398,599 B2 | 3/2013 | Bierman |
| 8,425,467 B1 | 4/2013 | Haak |
| 8,465,458 B2 | 6/2013 | Bierman |
| 8,496,625 B2 | 7/2013 | Brugger et al. |
| 8,500,698 B2 | 8/2013 | Kyvik et al. |
| 8,506,531 B2 | 8/2013 | Bierman |
| 8,540,680 B2 | 9/2013 | Burn |
| 8,579,863 B2 | 11/2013 | Scherr |
| 8,585,655 B2 | 11/2013 | Bierman |
| 8,608,704 B2 | 12/2013 | Bierman |
| 8,608,705 B2 | 12/2013 | Peters et al. |
| 8,608,706 B2 | 12/2013 | Davis et al. |
| 8,636,698 B2 | 1/2014 | Bierman et al. |
| 8,636,701 B2 | 1/2014 | Henry et al. |
| 8,641,678 B2 | 2/2014 | Bierman |
| 8,657,791 B2 | 2/2014 | Bierman et al. |
| 8,663,266 B1 | 3/2014 | Obsuth |
| 8,679,066 B2 | 3/2014 | Aviles |
| 8,679,067 B2 | 3/2014 | Wright |
| 8,684,976 B2 | 4/2014 | Bierman et al. |
| 8,708,967 B2 | 4/2014 | Bierman |
| 8,728,039 B2 | 5/2014 | Bierman et al. |
| 8,734,400 B2 | 5/2014 | Ciccone |
| 8,740,852 B2 | 6/2014 | Aviles |
| 8,747,360 B2 | 6/2014 | Peterson et al. |
| 8,795,237 B2 | 8/2014 | Vitaris et al. |
| 8,821,448 B2 | 9/2014 | Hawkins |
| 8,827,959 B2 | 9/2014 | Wright et al. |
| 8,827,960 B2 | 9/2014 | Haak |
| 8,834,424 B2 | 9/2014 | Parvatiyar et al. |
| 8,834,425 B2 | 9/2014 | Bracken et al. |
| 8,840,589 B2 | 9/2014 | Bierman et al. |
| 8,900,196 B2 | 12/2014 | Andino |
| 8,915,885 B2 | 12/2014 | Smith et al. |
| 8,945,062 B2 | 2/2015 | Waller |
| 8,969,649 B2 | 3/2015 | Leibowitz et al. |
| 8,986,257 B2 | 3/2015 | Rosenberg et al. |
| 9,017,290 B2 | 4/2015 | Peters et al. |
| 9,056,186 B2 | 6/2015 | Wright et al. |
| 9,061,122 B2 | 6/2015 | Bierman et al. |
| 9,067,013 B2 | 6/2015 | Wright et al. |
| 9,138,560 B2 | 9/2015 | Wright et al. |
| 9,155,866 B2 | 10/2015 | Bornhoft |
| 9,155,867 B2 | 10/2015 | Peterson et al. |
| 9,220,870 B2 | 12/2015 | Hyman et al. |
| 9,238,123 B2 | 1/2016 | Weadock et al. |
| 9,248,259 B2 | 2/2016 | Kyvik et al. |
| 9,248,260 B2 | 2/2016 | Khalaj |
| 9,314,596 B2 | 4/2016 | Rosenberg et al. |
| 9,327,098 B2 | 5/2016 | Kelvered et al. |
| 9,358,366 B2 | 6/2016 | Kyvik et al. |
| 9,415,191 B2 | 8/2016 | Aviles |
| 9,421,344 B2 | 8/2016 | Hyman et al. |
| 9,457,169 B2 | 10/2016 | Peterson et al. |
| 9,468,740 B2 | 10/2016 | Bierman et al. |
| 9,480,821 B2 | 11/2016 | Ciccone et al. |
| 9,492,640 B2 | 11/2016 | Rosenhan |
| 9,526,871 B2 | 12/2016 | Wright et al. |
| 9,550,043 B2 | 1/2017 | Rosenberg et al. |
| 9,561,348 B2 | 2/2017 | Bierman |
| 9,604,034 B2 | 3/2017 | Andino |
| 9,616,200 B2 | 4/2017 | Smith et al. |
| 9,642,987 B2 | 5/2017 | Bierman et al. |
| 9,694,130 B2 | 7/2017 | Andino et al. |
| 9,700,700 B2 | 7/2017 | Andino et al. |
| 9,731,097 B2 | 8/2017 | Andino et al. |
| 9,962,524 B2 | 5/2018 | Andino |
| 9,974,929 B2 | 5/2018 | Ciccone et al. |
| 9,993,619 B2 | 6/2018 | Bracken et al. |
| 10,245,415 B2 | 4/2019 | Andino et al. |
| 10,322,262 B2 | 6/2019 | Bracken et al. |
| 10,426,928 B2 | 10/2019 | Andino et al. |
| 10,537,714 B2 | 1/2020 | Andino et al. |
| 10,561,815 B2 | 2/2020 | Bierman et al. |
| 10,589,067 B2 | 3/2020 | Ciccone |
| 2001/0007061 A1 | 7/2001 | Bierman |
| 2001/0011164 A1 | 8/2001 | Bierman |
| 2001/0039399 A1 | 11/2001 | Bierman |
| 2002/0026152 A1 | 2/2002 | Bierman |
| 2002/0068904 A1 | 6/2002 | Bierman et al. |
| 2002/0099360 A1 | 7/2002 | Bierman |
| 2002/0133121 A1 | 9/2002 | Bierman |
| 2002/0143295 A1 | 10/2002 | Taylor et al. |
| 2002/0165493 A1 | 11/2002 | Bierman |
| 2002/0165494 A1 | 11/2002 | Bierman et al. |
| 2002/0187259 A1 | 12/2002 | Bierman |
| 2002/0188255 A1 | 12/2002 | Bierman et al. |
| 2002/0188257 A1 | 12/2002 | Bierman |
| 2003/0083625 A1 | 5/2003 | Bierman |

(56) References Cited

U.S. PATENT DOCUMENTS

| | | |
|---|---|---|
| 2003/0089374 A1 | 5/2003 | Bierman |
| 2003/0125668 A1 | 7/2003 | Bierman |
| 2003/0229313 A1 | 12/2003 | Bierman |
| 2004/0034330 A1 | 2/2004 | Bierman et al. |
| 2004/0102736 A1 | 5/2004 | Bierman |
| 2004/0138624 A1 | 7/2004 | Bierman |
| 2004/0167475 A1 | 8/2004 | Wright et al. |
| 2004/0199122 A1 | 10/2004 | Bierman et al. |
| 2004/0204684 A1 | 10/2004 | Bierman |
| 2004/0204685 A1* | 10/2004 | Wright ............ A61M 5/32 604/174 |
| 2004/0226565 A1 | 11/2004 | Bierman |
| 2005/0010173 A1 | 1/2005 | Bierman et al. |
| 2005/0027258 A1 | 2/2005 | Bierman et al. |
| 2005/0075610 A1 | 4/2005 | Bierman |
| 2005/0131351 A1 | 6/2005 | Bierman |
| 2005/0192539 A1 | 9/2005 | Bierman et al. |
| 2005/0192540 A1 | 9/2005 | Kessler |
| 2005/0215953 A1 | 9/2005 | Rossen |
| 2005/0263158 A1 | 12/2005 | Bierman |
| 2005/0273058 A1 | 12/2005 | Bierman |
| 2006/0041233 A1 | 2/2006 | Bowen |
| 2006/0064063 A1 | 3/2006 | Bierman |
| 2006/0084922 A1* | 4/2006 | Botha ............ A61M 5/158 604/174 |
| 2006/0089600 A1 | 4/2006 | Bierman et al. |
| 2006/0124133 A1 | 6/2006 | Bierman et al. |
| 2006/0129103 A1 | 6/2006 | Bierman et al. |
| 2006/0135944 A1 | 6/2006 | Bierman |
| 2006/0184127 A1 | 8/2006 | Bierman |
| 2006/0184128 A1 | 8/2006 | Bierman |
| 2006/0184129 A1 | 8/2006 | Bierman |
| 2006/0247577 A1 | 11/2006 | Wright |
| 2006/0264836 A1 | 11/2006 | Bierman |
| 2006/0270994 A1 | 11/2006 | Bierman |
| 2006/0270995 A1 | 11/2006 | Bierman |
| 2006/0276752 A1 | 12/2006 | Bierman et al. |
| 2007/0055205 A1 | 3/2007 | Wright et al. |
| 2007/0066958 A1 | 3/2007 | Wright |
| 2007/0068533 A1 | 3/2007 | Bierman et al. |
| 2007/0088329 A1 | 4/2007 | Bierman |
| 2007/0125483 A1 | 6/2007 | Barnett et al. |
| 2007/0142784 A1 | 6/2007 | Dikeman et al. |
| 2007/0149930 A1 | 6/2007 | Bierman |
| 2007/0156097 A1 | 7/2007 | Bierman |
| 2007/0167915 A1 | 7/2007 | Bierman |
| 2007/0173766 A1 | 7/2007 | Bierman |
| 2007/0173769 A1 | 7/2007 | Kessler |
| 2007/0219500 A1 | 9/2007 | Wright et al. |
| 2007/0265571 A1* | 11/2007 | Utterberg ............ A61M 25/02 604/174 |
| 2007/0265572 A1 | 11/2007 | Smith et al. |
| 2007/0276332 A1 | 11/2007 | Bierman |
| 2007/0276333 A1 | 11/2007 | Bierman |
| 2007/0276334 A1 | 11/2007 | Bierman et al. |
| 2007/0276335 A1 | 11/2007 | Bierman |
| 2007/0276336 A1 | 11/2007 | Bierman et al. |
| 2007/0282273 A1 | 12/2007 | Bierman |
| 2007/0287963 A1 | 12/2007 | Bierman |
| 2008/0027391 A1 | 1/2008 | Bierman |
| 2008/0027392 A1 | 1/2008 | Bierman |
| 2008/0027393 A1 | 1/2008 | Bierman |
| 2008/0027394 A1 | 1/2008 | Bierman |
| 2008/0039798 A1 | 2/2008 | Bierman |
| 2008/0077118 A1 | 3/2008 | Bierman |
| 2008/0097334 A1 | 4/2008 | Dikeman et al. |
| 2008/0132848 A1 | 6/2008 | Wright et al. |
| 2008/0154208 A1 | 6/2008 | Bierman |
| 2008/0200880 A1 | 8/2008 | Kyvik et al. |
| 2008/0249476 A1 | 10/2008 | Bierman et al. |
| 2008/0294119 A1 | 11/2008 | Schwartz et al. |
| 2009/0036835 A1 | 2/2009 | Bierman |
| 2009/0043260 A1 | 2/2009 | Bierman |
| 2009/0093766 A1 | 4/2009 | Bierman et al. |
| 2009/0093769 A1 | 4/2009 | Wright et al. |
| 2009/0137961 A1 | 5/2009 | Bracken |
| 2009/0137962 A1 | 5/2009 | Bracken et al. |
| 2009/0139061 A1 | 6/2009 | Nishtala |
| 2009/0143740 A1* | 6/2009 | Bierman ............ A61M 5/1415 604/177 |
| 2009/0143741 A1 | 6/2009 | Burn |
| 2009/0143742 A1 | 6/2009 | Bracken et al. |
| 2009/0143744 A1 | 6/2009 | Bierman et al. |
| 2009/0145440 A1 | 6/2009 | Bierman et al. |
| 2009/0182283 A1 | 7/2009 | Sloan |
| 2009/0198190 A1 | 8/2009 | Jensen et al. |
| 2009/0254040 A1 | 10/2009 | Bierman et al. |
| 2009/0259188 A1 | 10/2009 | Bierman et al. |
| 2009/0306603 A1 | 12/2009 | Bierman et al. |
| 2009/0326474 A1 | 12/2009 | Bierman et al. |
| 2010/0022962 A1 | 1/2010 | Bierman et al. |
| 2010/0100051 A1 | 4/2010 | Bierman |
| 2010/0114034 A1 | 5/2010 | Wright et al. |
| 2010/0137807 A1 | 6/2010 | Kessler |
| 2010/0179481 A1 | 7/2010 | Bierman et al. |
| 2010/0179482 A1 | 7/2010 | Wright et al. |
| 2010/0179483 A1 | 7/2010 | Wright et al. |
| 2010/0180900 A1 | 7/2010 | Talsma et al. |
| 2010/0222748 A1 | 9/2010 | Bierman et al. |
| 2010/0298777 A1 | 11/2010 | Nishtala |
| 2010/0298778 A1 | 11/2010 | Bracken et al. |
| 2010/0324491 A1* | 12/2010 | Bierman ............ A61M 25/02 604/174 |
| 2011/0021998 A1 | 1/2011 | Dikeman et al. |
| 2011/0054409 A1 | 3/2011 | Nishtala |
| 2011/0112483 A1 | 5/2011 | Smith et al. |
| 2011/0152778 A1 | 6/2011 | Gyrn |
| 2011/0166529 A1 | 7/2011 | LeLievre et al. |
| 2011/0178467 A1 | 7/2011 | Bierman et al. |
| 2011/0202010 A1 | 8/2011 | Bierman |
| 2011/0213310 A1 | 9/2011 | Bierman |
| 2011/0218498 A1 | 9/2011 | Bierman et al. |
| 2011/0230843 A1 | 9/2011 | Bierman et al. |
| 2011/0240034 A1 | 10/2011 | Ciccone |
| 2011/0245777 A1 | 10/2011 | Andino et al. |
| 2011/0257600 A1 | 10/2011 | Kessler |
| 2011/0264050 A1 | 10/2011 | Henry et al. |
| 2011/0282291 A1 | 11/2011 | Ciccone |
| 2011/0282294 A1 | 11/2011 | Dikeman et al. |
| 2011/0288487 A1 | 11/2011 | Wright et al. |
| 2011/0288489 A1 | 11/2011 | Bierman et al. |
| 2011/0295173 A1 | 12/2011 | Wright et al. |
| 2011/0295210 A1 | 12/2011 | Wright |
| 2011/0313362 A1 | 12/2011 | Bierman |
| 2011/0319830 A1 | 12/2011 | Peters et al. |
| 2012/0041377 A1 | 2/2012 | Haak |
| 2012/0041378 A1 | 2/2012 | Bierman |
| 2012/0046649 A1 | 2/2012 | Bierman |
| 2012/0053526 A1 | 3/2012 | Bierman et al. |
| 2012/0059328 A1 | 3/2012 | Dikeman et al. |
| 2012/0059329 A1 | 3/2012 | Bierman |
| 2012/0071833 A1* | 3/2012 | Hill ............ A61M 25/02 604/175 |
| 2012/0109070 A1 | 5/2012 | Elsamahy et al. |
| 2012/0123343 A1 | 5/2012 | Aviles |
| 2012/0136299 A1 | 5/2012 | Constantineau et al. |
| 2012/0136314 A1 | 5/2012 | Ciccone et al. |
| 2012/0143140 A1 | 6/2012 | Bierman et al. |
| 2012/0150117 A1 | 6/2012 | Andino |
| 2012/0184915 A1 | 7/2012 | Bierman et al. |
| 2012/0197202 A1 | 8/2012 | Wright et al. |
| 2012/0197205 A1 | 8/2012 | Peters |
| 2012/0215173 A1 | 8/2012 | Wright |
| 2012/0220947 A1 | 8/2012 | Dikeman et al. |
| 2012/0226237 A1 | 9/2012 | Russo |
| 2012/0232488 A1 | 9/2012 | Aviles |
| 2012/0232490 A1 | 9/2012 | Andino |
| 2012/0265147 A1 | 10/2012 | Andino et al. |
| 2012/0271237 A1 | 10/2012 | Andino |
| 2012/0271239 A1 | 10/2012 | Andino et al. |
| 2012/0271240 A1 | 10/2012 | Andino et al. |
| 2012/0316505 A1 | 12/2012 | Wright |
| 2013/0018322 A1 | 1/2013 | Wright et al. |
| 2013/0053785 A1 | 2/2013 | Parvatiyar et al. |

(56) References Cited

U.S. PATENT DOCUMENTS

| | | |
|---|---|---|
| 2013/0079723 A1 | 3/2013 | Andino et al. |
| 2013/0096507 A1 | 4/2013 | LeLievre |
| 2013/0138045 A1 | 5/2013 | Bierman |
| 2013/0138080 A1 | 5/2013 | Andino et al. |
| 2013/0150796 A1 | 6/2013 | Souza et al. |
| 2013/0150827 A1 | 6/2013 | Bracken et al. |
| 2013/0345639 A1 | 12/2013 | Spittler |
| 2014/0142538 A1 | 5/2014 | Hyman et al. |
| 2014/0188078 A1 | 7/2014 | Peters et al. |
| 2014/0249478 A1 | 9/2014 | Bierman et al. |
| 2014/0276542 A1 | 9/2014 | Ciccone |
| 2014/0276544 A1 | 9/2014 | Aviles |
| 2014/0276658 A1 | 9/2014 | Ward |
| 2014/0303574 A1 | 10/2014 | Knutson |
| 2014/0343501 A1 | 11/2014 | Bierman et al. |
| 2015/0086741 A1 | 3/2015 | Karim et al. |
| 2015/0088076 A1 | 3/2015 | Andino |
| 2015/0112270 A1 | 4/2015 | Smith et al. |
| 2015/0133891 A1 | 5/2015 | Rosenhan |
| 2015/0224285 A1 | 8/2015 | Howell et al. |
| 2015/0224286 A1 | 8/2015 | Teh et al. |
| 2015/0265808 A1 | 9/2015 | Bierman et al. |
| 2015/0367102 A1 | 12/2015 | Andino et al. |
| 2016/0008577 A1 | 1/2016 | Wright et al. |
| 2016/0015932 A1 | 1/2016 | Catudal |
| 2016/0067451 A1 | 3/2016 | Kyvik et al. |
| 2016/0184554 A1 | 6/2016 | Rosenberg et al. |
| 2016/0193452 A1 | 7/2016 | Hanson et al. |
| 2016/0206857 A1 | 7/2016 | Mitchell et al. |
| 2016/0317786 A1 | 11/2016 | Friedrich |
| 2017/0043130 A1 | 2/2017 | Jones et al. |
| 2017/0043131 A1 | 2/2017 | Ciccone et al. |
| 2017/0216556 A1 | 8/2017 | Bierman et al. |
| 2017/0296788 A1 | 10/2017 | Andino et al. |
| 2017/0296789 A1 | 10/2017 | Andino et al. |
| 2019/0247625 A1 | 8/2019 | Bracken et al. |
| 2020/0030578 A1 | 1/2020 | Andino et al. |

FOREIGN PATENT DOCUMENTS

| | | |
|---|---|---|
| WO | 9610435 A1 | 4/1996 |
| WO | 1997/005920 A1 | 2/1997 |
| WO | 9715337 A1 | 5/1997 |
| WO | 9715342 A1 | 5/1997 |
| WO | 1998/032481 A1 | 7/1998 |
| WO | 9853872 A1 | 12/1998 |
| WO | 1999/020334 A1 | 4/1999 |
| WO | 1999/025399 A1 | 5/1999 |
| WO | 9955409 A1 | 11/1999 |
| WO | 2000/010637 A1 | 3/2000 |
| WO | 2001/062328 A1 | 8/2001 |
| WO | 2001/068180 A1 | 9/2001 |
| WO | 01/91847 A2 | 12/2001 |
| WO | 2002/011786 A2 | 2/2002 |
| WO | 2002/056958 A2 | 7/2002 |
| WO | 2003/092781 A2 | 11/2003 |
| WO | 2004016309 A2 | 2/2004 |
| WO | 2004/030741 A2 | 4/2004 |
| WO | 2005/081882 A2 | 9/2005 |
| WO | 06087755 A1 | 8/2006 |
| WO | 2006/113620 A2 | 10/2006 |
| WO | 2007/011596 A2 | 1/2007 |
| WO | 2007/035605 A2 | 3/2007 |
| WO | 2007024900 A2 | 3/2007 |
| WO | 2007028007 A2 | 3/2007 |
| WO | 2007/075491 A2 | 7/2007 |
| WO | 2007/082093 A2 | 7/2007 |
| WO | 2007117655 A2 | 10/2007 |
| WO | 2008051810 A2 | 5/2008 |
| WO | 2008/116119 A2 | 9/2008 |
| WO | 2009/003137 A1 | 12/2008 |
| WO | 2008151047 A1 | 12/2008 |
| WO | 09/032008 A2 | 3/2009 |
| WO | 2009/035450 A1 | 3/2009 |
| WO | 2009055739 A1 | 4/2009 |
| WO | 2010/002393 A1 | 1/2010 |
| WO | 2010/016837 A1 | 2/2010 |
| WO | 2010/033109 A1 | 3/2010 |
| WO | 2010/033858 A1 | 3/2010 |
| WO | 2010102153 A1 | 9/2010 |
| WO | 10/132837 A1 | 11/2010 |
| WO | 2010/132843 A1 | 11/2010 |
| WO | 2011025478 A1 | 3/2011 |
| WO | 2011/044256 A1 | 4/2011 |
| WO | 2011/044259 A1 | 4/2011 |
| WO | 2011/044293 A1 | 4/2011 |
| WO | 2011/109542 A1 | 9/2011 |
| WO | 2012/015440 A1 | 2/2012 |
| WO | 2014/149668 A1 | 9/2014 |
| WO | 16164598 A2 | 10/2016 |

OTHER PUBLICATIONS

PCT/US2020/028583 filed Apr. 16, 2020 International Search Report and Written Opinion dated Jul. 27, 2020.

U.S. Appl. No. 16/851,031, filed Apr. 16, 2020 Non-Final Office Action dated Nov. 23, 2021.

U.S. Appl. No. 16/851,031, filed Apr. 16, 2020 Notice of Allowance dated May 3, 2022.

\* cited by examiner

CATHETER SECUREMENT DEVICE INCLUDING A GUIDING NOSE

CROSS-REFERENCE TO RELATED APPLICATIONS

This application claims the benefit of U.S. Provisional Patent Application No. 62/336,496, filed May 13, 2016, and titled "Catheter Securement Device Including Guiding Nose," which is incorporated herein by reference in its entirety.

BRIEF SUMMARY

Briefly summarized, embodiments of the present invention are directed to a securement device configured to secure an external portion of a medical device to the skin surface of a patient after an internal portion of the device has been placed in the patient. The securement device includes a catheter retainer that is employed to securely but removably retain the external portion of the catheter assembly in place. In one embodiment, the catheter retainer is attached to a base, such as an adhesive pad that adhesively attaches to the skin surface, to form the securement device, also referred to herein as a catheter retainer system or catheter retainer assembly.

In one embodiment, therefore, a retainer for retaining an external portion of a medical device after insertion of an internal portion of the medical device into a body of a patient via a skin insertion site comprises a body defining a channel configured to receive therein a portion of the external portion of the medical device, and at least one foot extending from the body. The foot is configured to stabilize the retainer with respect to a skin surface of the patient. The retainer body further includes a nose that is configured to deflect a strain relief portion (or other portion) of a catheter assembly (for instance) toward the skin insertion site. Such deflection lessens the incidence of kinking in the medical device, such as a catheter tube, proximate the skin insertion site.

These and other features of embodiments of the present invention will become more fully apparent from the following description and appended claims, or may be learned by the practice of embodiments of the invention as set forth hereinafter.

BRIEF DESCRIPTION OF THE DRAWINGS

A more particular description of the present disclosure will be rendered by reference to specific embodiments thereof that are illustrated in the appended drawings. It is appreciated that these drawings depict only typical embodiments of the invention and are therefore not to be considered limiting of its scope. Example embodiments of the invention will be described and explained with additional specificity and detail through the use of the accompanying drawings in which.

DETAILED DESCRIPTION OF SELECTED EMBODIMENTS

Reference will now be made to figures wherein like structures will be provided with like reference designations. It is understood that the drawings are diagrammatic and schematic representations of exemplary embodiments of the present invention, and are neither limiting nor necessarily drawn to scale.

For clarity it is to be understood that the word "proximal" refers to a direction relatively closer to a clinician using the device to be described herein, while the word "distal" refers to a direction relatively further from the clinician. For example, the end of a catheter placed within the body of a patient is considered a distal end of the catheter, while the catheter end remaining outside the body is a proximal end of the catheter. Also, the words "including," "has," and "having," as used herein, including the claims, shall have the same meaning as the word "comprising."

Embodiments of the present invention are generally directed to a securement device that is configured to secure an external portion of a catheter assembly to the skin surface of a patient after an internal portion of the catheter assembly has been placed in the patient to establish vascular access, or for some other suitable purpose. The securement device includes a catheter retainer that is employed to securely but removably retain the external portion of the catheter assembly in place. In one embodiment, the catheter retainer is attached to a base, such as an adhesive pad that adhesively attaches to the skin surface, to form the securement device, also referred to herein as a catheter retainer system or catheter retainer assembly. It is appreciated that, though the discussion to follow focuses on a midline catheter, catheters and other tubular or elongate medical devices that are configured for attachment or may be attached to a skin surface of the patient may also benefit from the teachings herein, including dialysis catheters, Foley and urinary catheters, feeding tubes, balloon catheters, PIVs, etc.

Figure 1A:
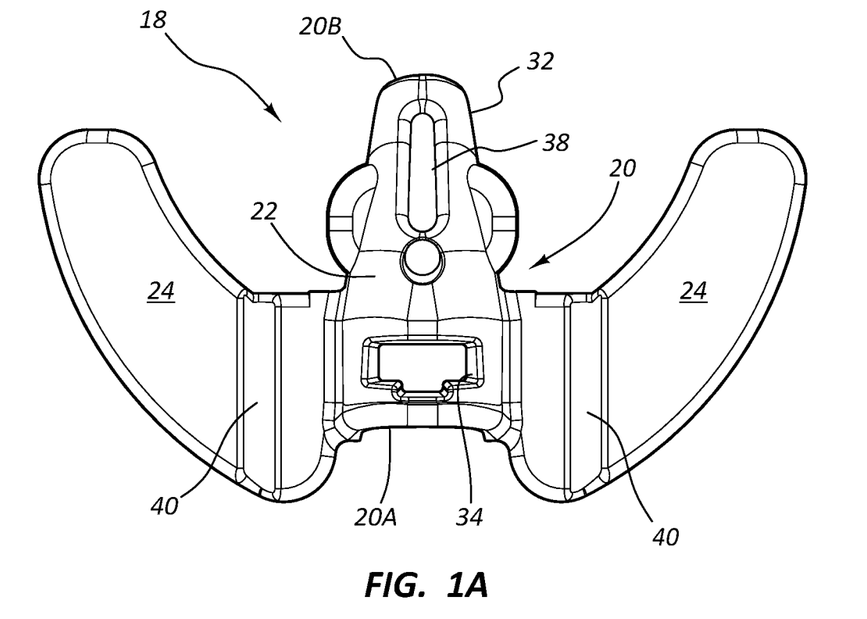
FIGS. 1A-1C are: various views of a catheter retainer according to one embodiment.
Figure 1B:
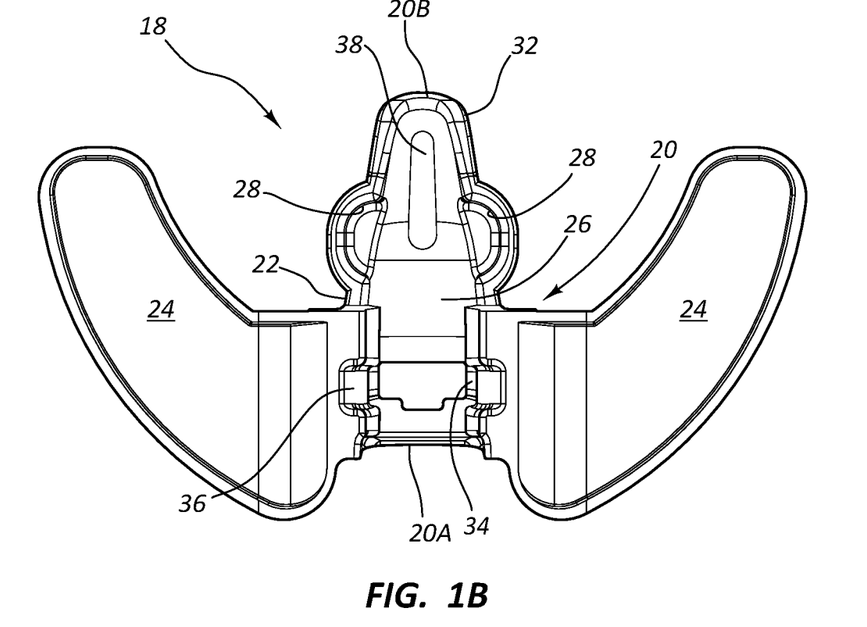
Figure 1C:
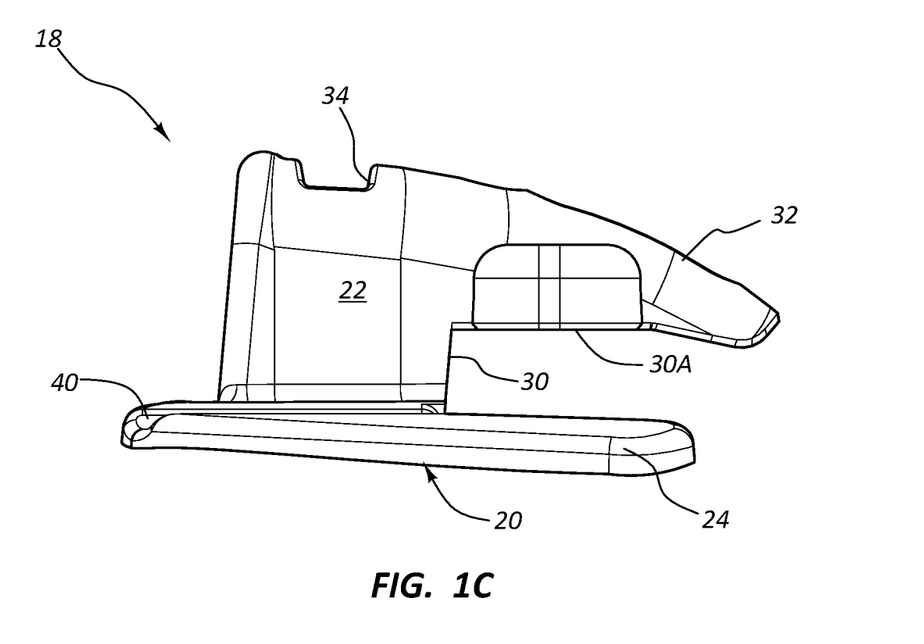

Reference is made to FIGS. 1A-1C in describing various details of a catheter retainer (also "retainer"), generally designated at 18, according to one embodiment. The retainer 18 includes a body 20 extending between a proximal end 20A and a distal end 20B. The body 20 includes a central portion 22 and two feet 24 that extend from the central portion. As shown, the feet 24 each arcuately sweep distally to provide a stable base for the retainer 18 and reduce rocking of the retainer when the securement device is positioned on the skin of the patient. As will be seen, the feet 24 are configured to attach to adhesive anchor pads for adhesively attaching the retainer to a skin surface of a patient. In addition, each of the feet 24 includes a longitudinally extending living hinge 40 that enables the feet to bend to conform to the contour of the skin surface of the patient when the retainer, as part of a below-discussed securement device, is disposed on the patient. For instance, the living hinges 40 enable the feet 24 to bend around the skin surface of a patient arm in one embodiment. Note that the size and position of the living hinges 40 can vary from what is shown and described herein. Also, more than one living hinge can be included on each foot 24 to further enhance bending ability of the feet.

The retainer body 20 defines a longitudinally extending channel 26 sized and configured to receive therein portions of a strain relief 48 and a hub 46 of a catheter assembly (also "catheter") 42, as will be discussed below in connection with FIGS. 2A-2D. The channel 26 includes art opening, as seen in the bottom view of FIG. 1B, and the body 20 is elastically deformable sufficient to enable the catheter to be retained in the channel 26 in a snap-fit configuration in the present embodiment. Though a variety of suitable materials can be employed, in the present embodiment the retainer body 20 is composed of polycarbonate. Note that the particular size, shape, and configuration of the channel 26 can vary to accommodate the shape and configuration of a particular catheter or other medical device. Details regarding the catheter shown and described herein can be found in U.S. patent application Ser. No. 14/702,580, filed May 1, 2015, and entitled "Catheter Placement Device Including Guidewire and Catheter Control Elements," which is incorporated herein by reference in its entirety.

Two pockets 28 are included with the channel 26 and are sized and positioned to receive therein two nubs 49 of the catheter strain relief 48 (FIGS. 2B, 2C), which assists in preventing undesired rotation of the catheter 42 within the retainer 18 after placement therein.

FIG. 1C shows that the retainer body 20 further defines a notch 30 that provides a space to be occupied by a skin-placed dressing when the retainer 18 is placed proximate the skin surface of the patient. An upper surface 30A of the notch 30 is configured at a predetermined height above the skin surface of the patient such that a slight compression of the skin-placed dressing is imposed by the retainer body 20 when the securement device is placed on the skin. Again, the size, shape, and configuration of the notch 30 can vary according to the type of dressing to be received therein. In one embodiment, the skin-placed dressing is an antimicrobial disk 60 (FIG. 3A, 3B), such as a GUARDIVA® antimicrobial haemostatic dressing sold by Bard Access Systems, Inc. of Salt Lake City, Utah (also referred to herein as a "GUARDIVA® dressing"). A variety of other dressings and components can be included instead of or in addition to the skin-placed dressing.

In the present embodiment, the retainer body 20 further includes a nose 32 that is angled downward so as to constrain the catheter strain relief 48 of the catheter hub 46 (FIG. 2A) disposed within the channel 26 and deflect it in a slightly downward direction. The angle of the downward bend imposed by the nose 32 is predetermined and can vary according to various factors. This deflection of the catheter strain relief 48 in turn helps to provide a non-abrupt direction change for the catheter tube 44 as it enters the skin insertion site on the patient skin surface, thus avoiding undesired kinking of the catheter tube 44 or the strain relief 48. In one embodiment, the magnitude of the angle change imposed on the catheter strain relief 48/catheter tube 44 by the angled nose 32 is about 14 degrees, but it is appreciated that the nose can be configured to impose other angles. Also, note that other portions of the external portion of the catheter (or other elongate/suitable medical device) can be deflected by the nose 32, including the hub and the catheter tube. As such, the description herein should not be considered limiting.

FIG. 1C shows that the nose 32, together with corresponding surfaces of the retainer body 20 (including portions of the body that define the pockets 28) cooperate to define the upper surface 30A of the notch 30. Indeed, the downward angle of the nose 30 assists in providing the predetermined slight compression on the skin-placed dressing when disposed in the notch.

Figure 2A:
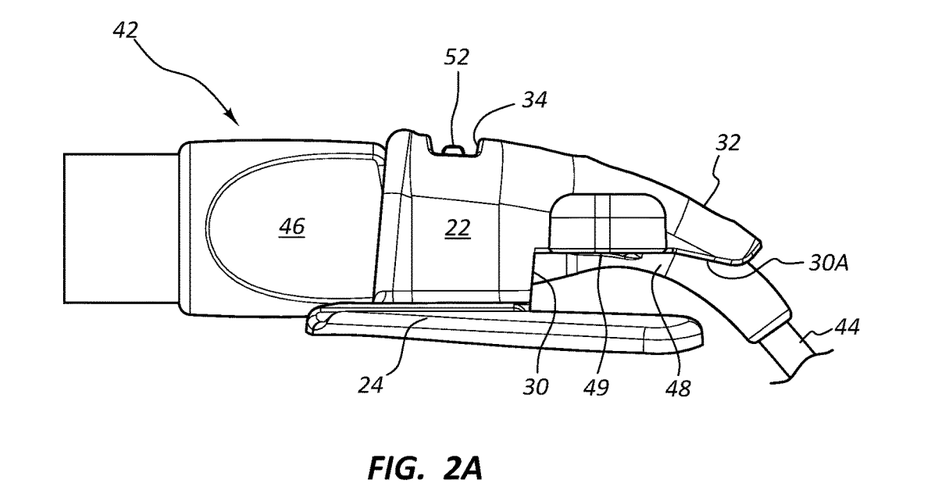
FIGS. 2A-2D show the catheter retainer of FIGS. 1A-1C engaged with a catheter assembly.
Figure 2B:
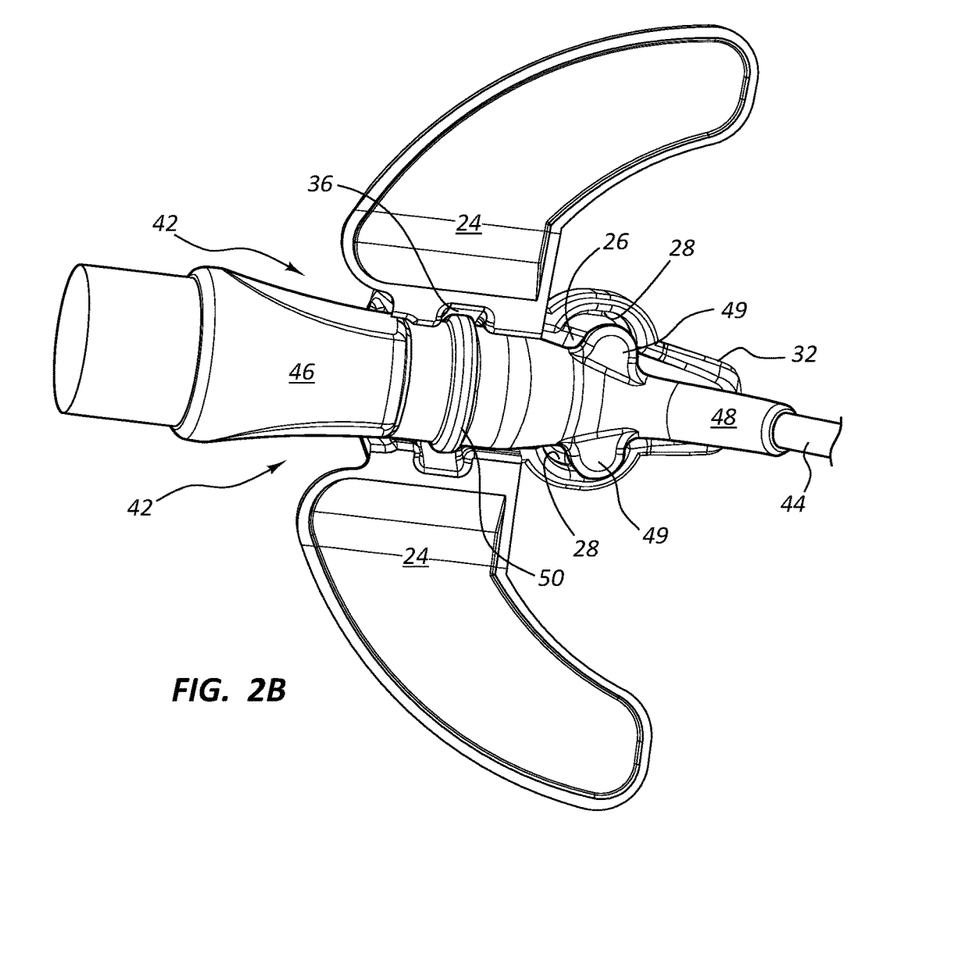

FIGS. 2A-2D depict various views of the catheter 42 and its insertion into the retainer 18 according to one embodiment. As shown, the catheter 42 is inserted into the retainer by a portion of the hub 46 and strain relief 48 being received into the channel 26 of the retainer body 20. FIG. 2B shows the insertion of the catheter 42 in this manner such that the nubs 49 of the strain relief 48 are received into the pockets 28 of the retainer body channel 26. As mentioned, the retainer body 20 is sufficiently resilient to deform sufficient to receive the catheter hub 46 and strain relief 48 therein in a snap-fit configuration.

Figure 2C:
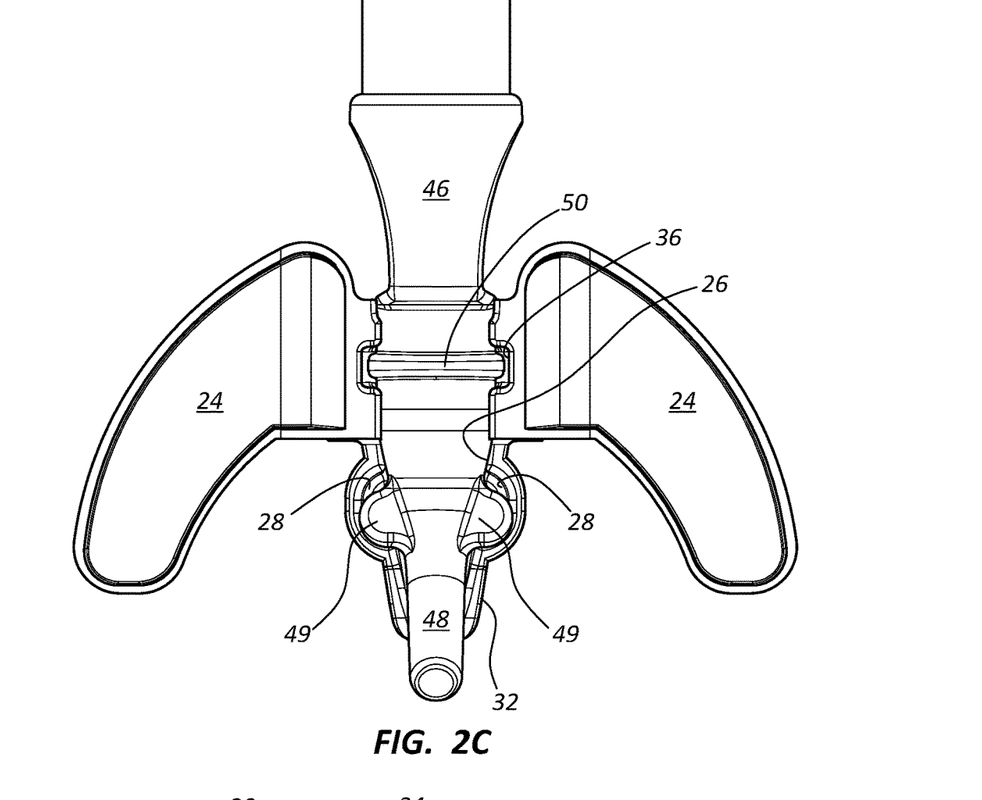
Figure 2D:
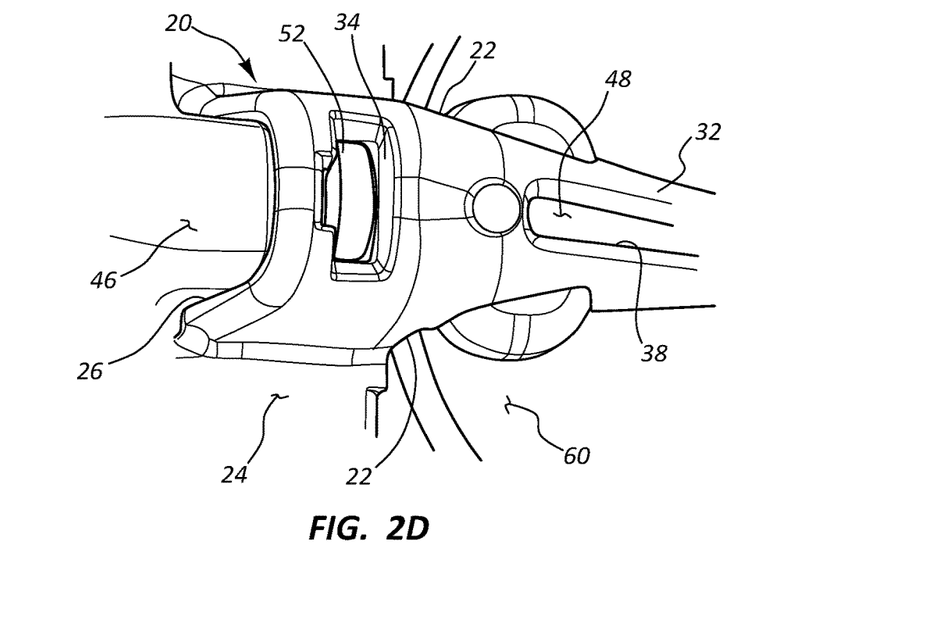

FIGS. 2B-2D show that the catheter hub 46 includes a radially extending alignment ring 50 and a lock tab 52 extending further therefrom. The alignment ring 50 is configured to be received within a lock channel 36 of the retainer body channel 26 when the catheter hub 46 is received with the channel 26. When this occurs, the lock tab 52 is configured to be received into a lock window 34 defined by the retainer body 20. This in turn prevents unintended rotation of the catheter hub 46 and within the retainer body channel 26 about its longitudinal axis when received therein, as well as preventing related kinking of the catheter tube 44 when undesired rotation is experienced. Note that in one embodiment the lock tab 52 can be colored a color different from surrounding catheter assembly structure so as to highlight it and provide easy confirmation to a clinician as to when the lock tab has been received in the lock window 34.

In the present embodiment, unintended catheter hub rotation is further assisted by the receipt of the strain relief nubs 49 within the pockets 28 of the retainer body channel 26. FIG. 2D further shows that the retainer body defines a view window 38 through which the strain relief 48 of the catheter can be viewed. In addition to these, other modes for preventing unintended rotation of the catheter hub within the retainer body channel are also contemplated. It is further appreciated that the engagement of the nubs 49 within the pockets 28 of the retainer body channel 26, together with the engagement of the alignment ring 50 with the lock channel 26, assists in preventing undesired movement of the catheter assembly 42 along its longitudinal axis while the catheter is received within the retainer. Note that the lock channel 36 is tapered at the point of entrance of the alignment ring 50 to ease the insertion of the alignment ring therein.

Figure 3A:
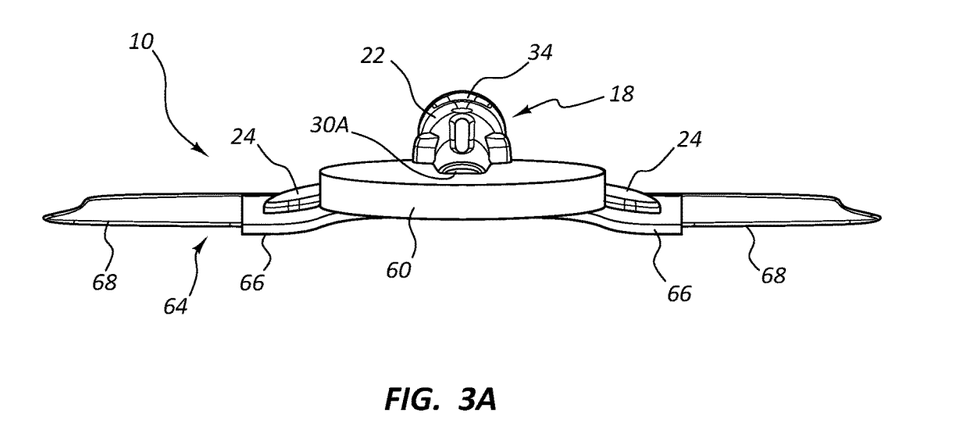
FIGS. 3A and 3B depict various views of a catheter retainer assembly according to one embodiment.
Figure 3B:
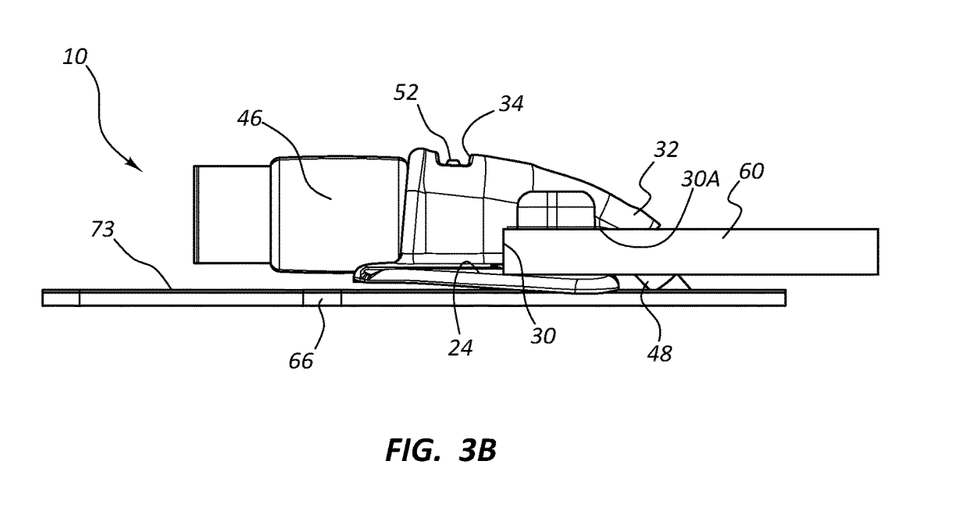

FIGS. 3A and 3B depict the retainer 18 incorporated into a securement device 10 as an assembly for retaining a portion of a catheter assembly or other suitable medical device in a secured position on or proximate the skin surface of the patient. As shown, the securement device 10 is shown in the configuration as applied to the skin surface of a patient and includes the retainer 18 as described above retaining the hub 46/strain relief 48 of the catheter assembly 42 as described above. The retainer 18 is permanently affixed (such as via adhesive or mechanical fixation) to a pair of adhesive anchor pads 64, themselves including a central foam portion 66 and an overlying fabric portion 68 such as polyester fiber. Adhesive is placed on the bottom, skin-facing surface of the anchor pads 64 and a release liner placed on the adhesive surface. The anchor pads 64 extend out from either side of the bottom opening of the retainer body channel 26 so as to not interfere with the insertion and removal of the catheter hub 46/strain relief 48 into and from the retainer body channel 26. In the present embodiment, the anchor pads 64 are permanently affixed to the bottom, skin-facing surfaces of the two feet 24. The anchor pads can, of course, include various sizes, shapes, and configurations. Note that the foam portion 66 and the fabric portion 68 can include other materials in other embodiments, such as nonwoven materials, synthetic and natural materials, etc.

FIGS. 3A and 3B further show an antimicrobial disk 60 as an example of a skin-placed dressing, as described further above, in place with respect to the securement device 10. The antimicrobial disk 60 is positioned about the skin insertion site to prevent the occurrence of infection at/via the insertion site and, as already mentioned, the retainer body 20 defines the notch 30 to provide space in which a corresponding portion of the antimicrobial disk 60 can reside. Also, as mentioned, the upper surface 30A of the notch 30 is sized to desirably provide slight compression on the antimicrobial disk. As mentioned, in one embodiment the antimicrobial disk 60 is a GUARDIVA® antimicrobial haemostatic dressing. The antimicrobial disk 60 is understood to include any one of a variety of components placed at or near the insertion site of the catheter (or other medical device), including dressings, pads, antimicrobial devices, bandages, etc.

FIGS. 2A, 2C, and 3B depict the manner of deflection (as discussed above) of the strain relief 48 and catheter tube 44 downward toward the skin insertion site so as to prevent kinking of the catheter tube proximal and/or distal to the skin insertion site. FIG. 3B further depicts the strain relief 48 passing through a central hole of the antimicrobial disk 60, directing the catheter tube 44 to the insertion site in a desirable low-kink configuration. The inclusion of the notch 30 in the retainer body for the antimicrobial disk 60, together with the downward-angling nose 32 for angling the catheter strain relief 48 and catheter tube 44 toward the skin insertion site, in turn enables the strain relief 48 and hub 46 of the catheter 42 to be positioned relatively closer to the insertion site of the catheter without kinking than would otherwise be possible. Note that in the configuration shown in FIG. 3B when the securement device 10 is placed on a skin surface of the patient, the hub 46 of the catheter assembly is substantially parallel to the skin surface while the strain relief 48 and external portion of the catheter tube 44 proximal to the skin insertion site 72 (FIGS. 4A, 4B) is angled downward, as described above. Maintenance of the catheter hub 46 in a substantially parallel position with respect to the skin surface by the securement device 10 in turn helps to prevent cantilevered movement of the catheter hub on the securement device and undesired movement of the catheter tube with respect to the skin insertion site.

Figure 4A:
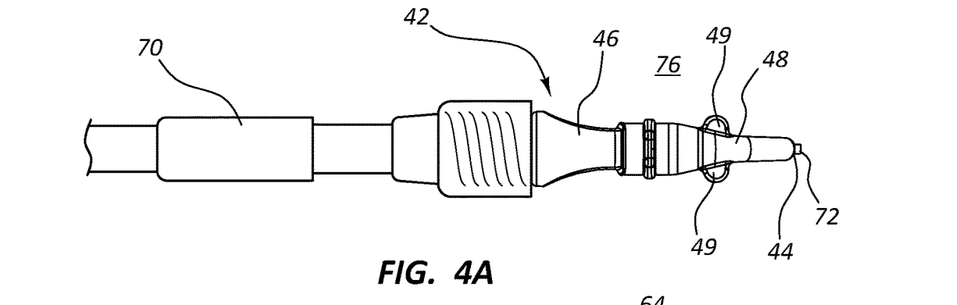
FIGS. 4A-4C depict various stages of insertion of a catheter assembly and use of a catheter retainer assembly according to one embodiment.
Figure 4B:
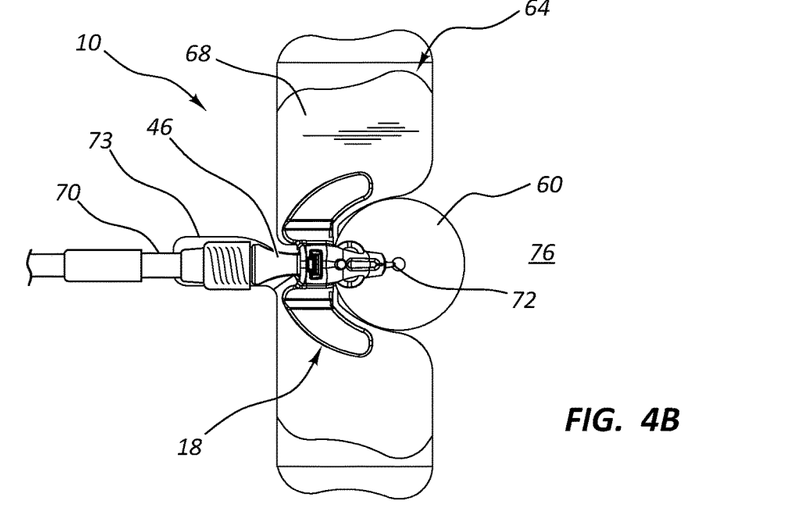
Figure 4C:
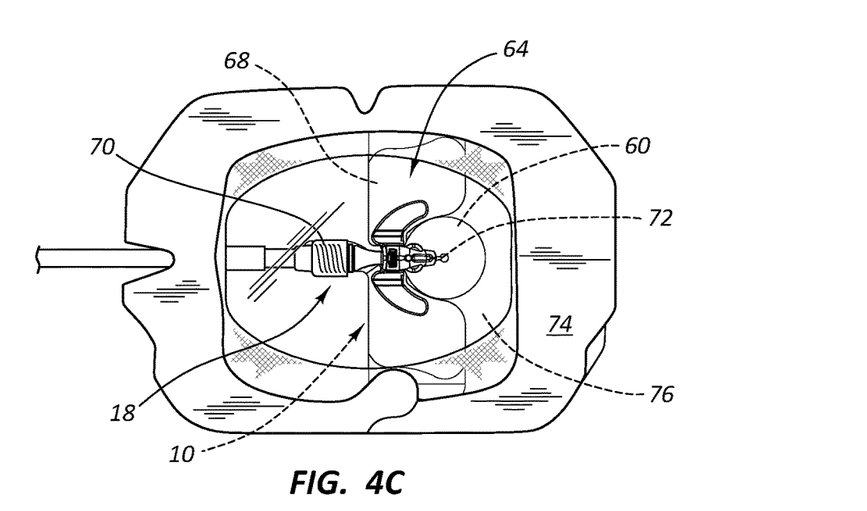

FIGS. 4A-4C depict various stages showing the application of the securement device 10 in securing the catheter assembly 42 to a patient, according to one embodiment. FIG. 4A shows an external portion of the catheter assembly 42, including the hub 46, the strain relief 48, and a proximal portion of the catheter tube 44 passing through an insertion site 72 on a skin surface 76. An extension set 70 is shown attached to the hub 46.

FIG. 4B shows the antimicrobial disk 60 disposed about the insertion site 72 on the skin surface, such as a portion of the patient arm. The insertion device 10 is also shown, positioned over the catheter such that the hub 46 and strain relief 48 are received into the channel 26 thereof in a snap-fit arrangement. The adhesive anchor pads 64 are also adhered to the skin surface 76 on either side of the retainer 18 (after removal of a release layer covering the adhesive) to secure the catheter assembly 42 to the skin surface and to prevent inadvertent removal of the catheter tube 44 from the insertion site. A non-adhesive comfort pad 73 extends from one of the anchor pads to be interposed between the catheter assembly 42 and the skin surface 76 so as to prevent abrasion therebetween. The comfort pad 73 in the present embodiment includes polyester fiber layer overlying a foam layer and includes a perforation in one embodiment so as to enable its removal from the insertion device when not desired. Note that the anchor pads 64 and the feet 24 are shaped to enable the antimicrobial disk 60 to be received into the notch 30 of the retainer body in the manner shown in FIGS. 3A and 3B.

Figure 8:
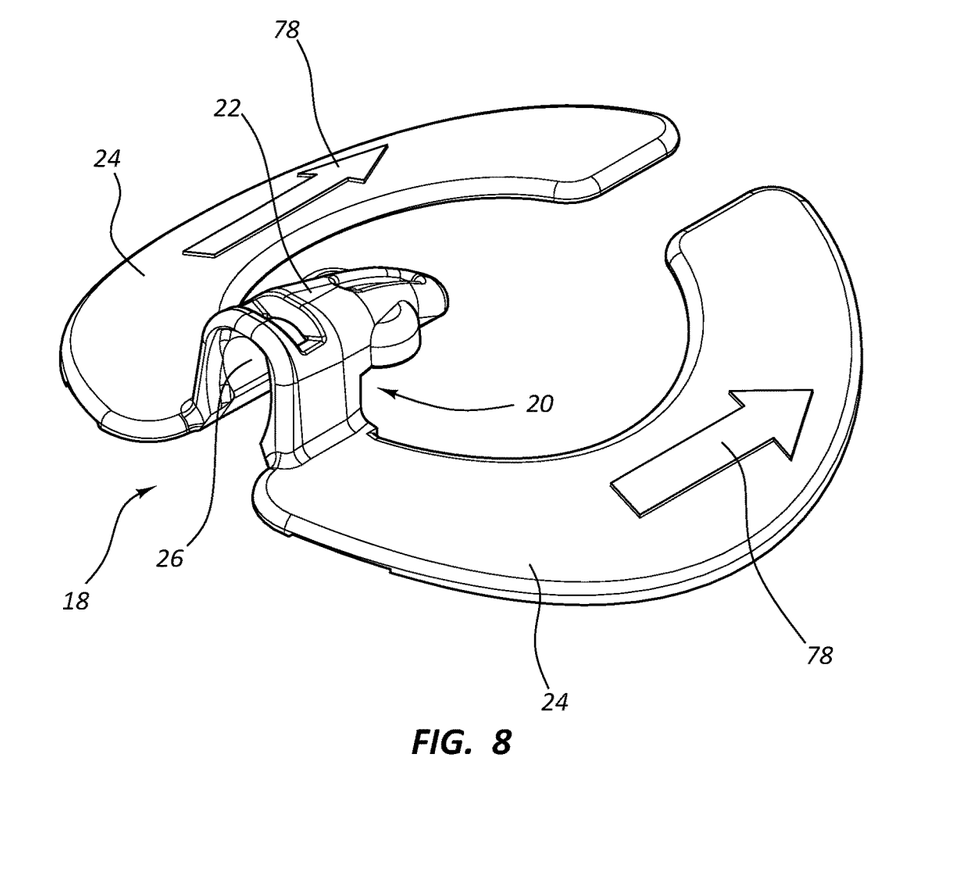
FIG. 8 is a top view of a catheter retainer according to one embodiment.

Note also that the arcuately and distally extending feet 24, together with the adhesive attachment to the patient skin surface 76 of the anchor pads 64 to points distally past and to either side of the insertion site 72, enables the securement device 10 to move in concert with the skin surface 76 proximate the insertion site 72, thus further reducing chances of kinking of the catheter tube 44 or undesired relative movement of the catheter tube with respect to the insertion site. In light of this, it is appreciated that the feet 24 can extend in different shapes and to different distances with respect to the central portion 22 of the retainer body 20. An example of this is shown in FIG. 8, which depicts the feet 24 arcuately extending distally with respect to the central portion 22 of the retainer body 20 to form a near circular footprint about the insertion site for the catheter to enhance the ability of the securement device and the skin surface to move in concert with one another and prevent relative movement between the catheter tube and the insertion site. These and other possible foot configurations are therefore contemplated.

In FIG. 4C, an adhesive cover dressing 74 is adhered to the skin surface 76 to cover the aforementioned components and protect them from contamination. It is appreciated that different or additional components can be employed in concert with the catheter assembly and insertion device shown and described herein.

Figure 5A:
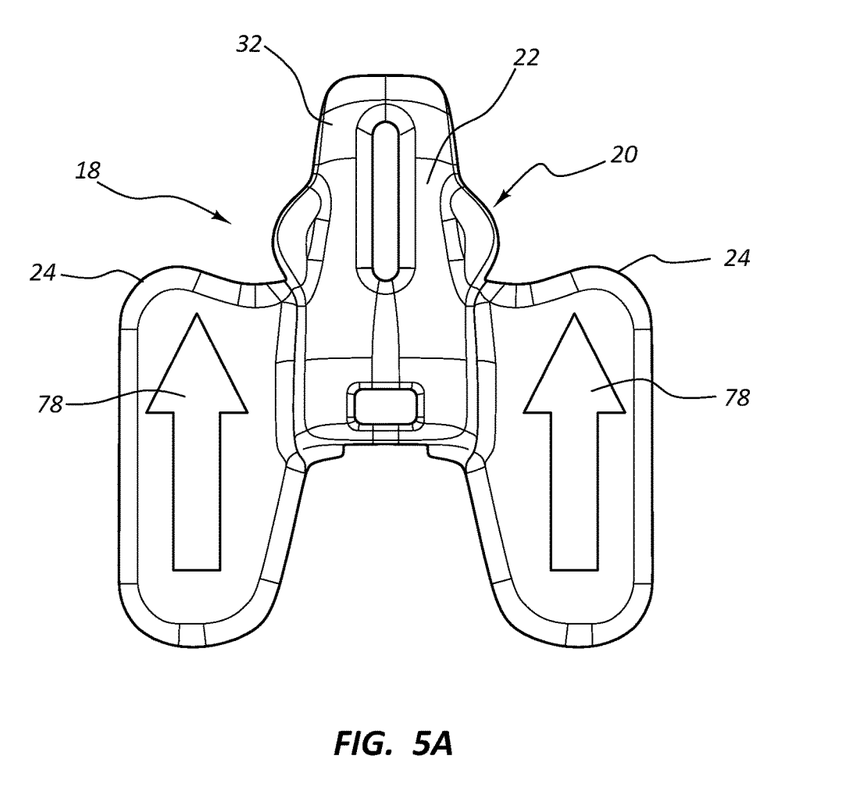
FIGS. 5A and 5B depict various views of a catheter retainer according to one embodiment.
Figure 5B:
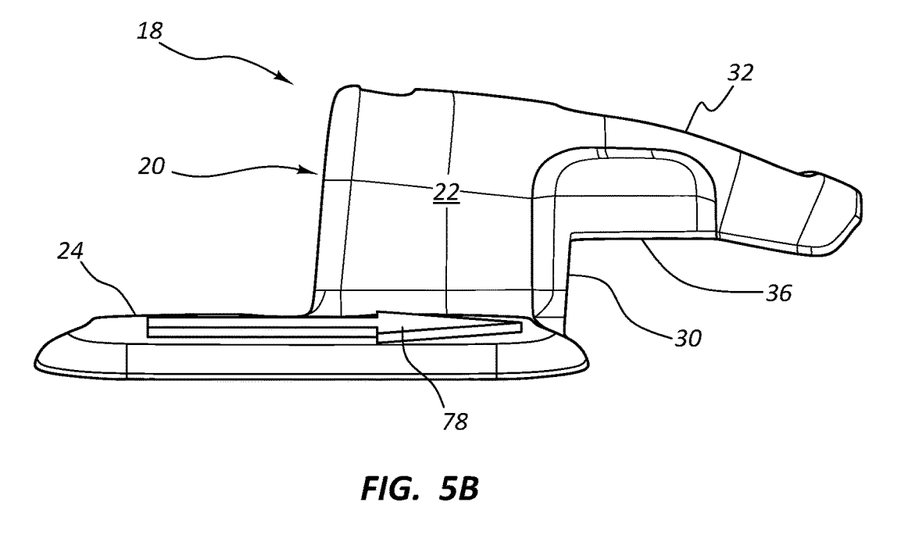

FIGS. 5A and 5B depict details of the retainer 18 according to another embodiment wherein the feet 24 are shaped so as to extend more proximally with respect to the central portion 22 of the retainer body 20. Guidance arrows 78 are also included to assist the clinician in knowing the proper direction for placement of the retainer 18.

Figure 6:
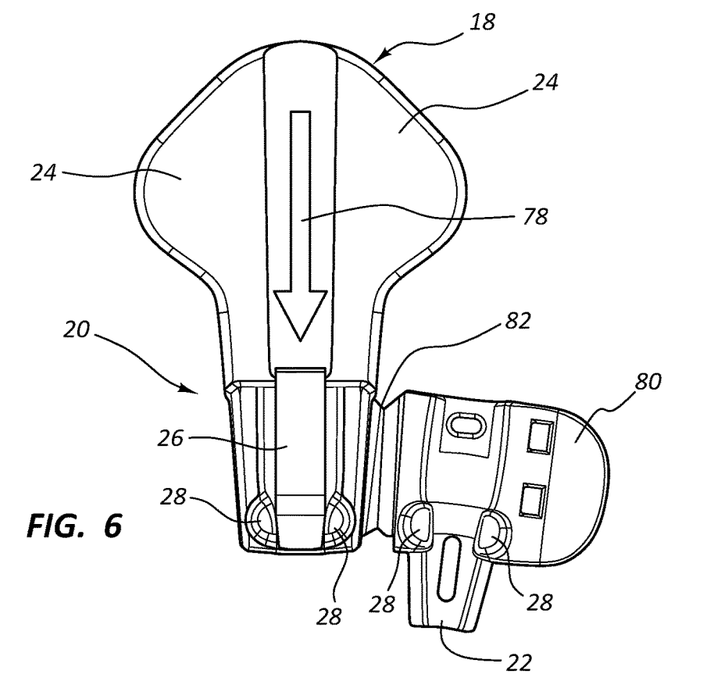
FIG. 6 is a top view of a catheter retainer according to one embodiment.
Figure 7:
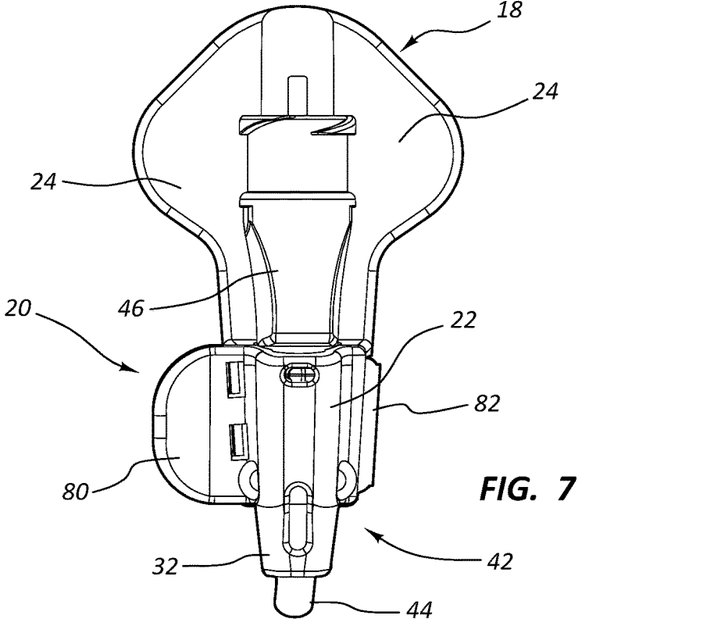
FIG. 7 is a top view of the catheter retainer of FIG. 6 engaged with a catheter assembly according to one embodiment.

FIGS. 6 and 7 depict the retainer 18 according to yet another embodiment, wherein the feet 24 extend proximally to the retainer body 20 to provide stability for the inserted catheter 42. The retainer body 20 further includes a base portion that is configured to be disposed underneath the entirety of the strain relief 48 and hub 46 of the catheter 42 so as to prevent abrasion of the patient skin by these or other components attached to the catheter. The retainer 18 of further includes a cap 80 that covers a portion of the channel 26, the cap being attached to the retainer body 20 by a living hinge 82, or other suitable attachment mode. As with the previous embodiment the guidance arrow 78 is provided on the retainer 18.

Embodiments of the invention may be embodied in other specific forms without departing from the spirit of the present disclosure. The described embodiments are to be considered in all respects only as illustrative, not restrictive. The scope of the embodiments is, therefore, indicated by the appended claims rather than the foregoing description. All changes that come within the meaning and range of equivalency of the claims are to be embraced within their scope.

Embodiments of the invention may be embodied in other specific forms without departing from the spirit of the present disclosure. The described embodiments are to be considered in all respects only as illustrative, not restrictive. The scope of the embodiments is, therefore, indicated by the appended claims rather than by the foregoing description. All changes that come within the meaning and range of equivalency of the claims are to be embraced within their scope.

What is claimed is:

1. A retainer and medical device system, comprising:
a medical device comprising:
an external a portion having a catheter hub, a strain relief, and portion of a catheter tube; and
an internal portion for insertion into a vasculature of a patient via a skin insertion site; and
a retainer having a body comprising:
a proximal arched portion defining a channel opening and engaging a portion of the catheter hub of the medical device;
a central arched portion connected to the proximal arched portion, the central arched portion having a continuous outer surface extending from a first base on a first side to a second base on a second side, the first base and the second base extending over a first plane, the proximal arched portion maintaining a central axis of the catheter hub parallel to the first plane;
a first foot extending from the first base;
a second foot extending from the second base;
a lock window positioned through a top surface of the central arched portion; and
a nose portion connected to the central arched portion in a fixed relationship, the nose portion having a continuous outer surface angled from the central arched portion toward the skin insertion site, the nose portion engaging at least the strain relief of the medical device to deflect a central axis of the strain relief at an angle relative to the central axis of the catheter hub, toward the skin insertion site.

2. The retainer and medical device system as defined in claim 1, wherein the nose portion, the central arched portion, and the proximal arched portion together define a covered channel.

3. The retainer and medical device system as defined in claim 1, wherein the medical device is a catheter assembly and the body of the retainer and medical device system is configured to retain a portion of the catheter assembly against a skin surface of the patient.

4. The retainer and medical device system as defined in claim 3, wherein the lock window is configured to receive an alignment ring of the catheter assembly.

5. The retainer and medical device system as defined in claim 4, wherein the body of the retainer and medical device system further comprises a first pocket extending from a first side of the nose portion and a second pocket extending from a second side of the nose portion, the first pocket is configured to receive a first strain relief nub of the strain relief of the catheter assembly in a snap-fit arrangement, and the second pocket is configured to receive a second strain relief nub of the strain relief of the catheter assembly in a snap-fit arrangement.

6. The retainer and medical device system as defined in claim 1, wherein the nose portion is configured to deflect the central axis of the strain relief of the medical device about 14 degrees with respect to the central axis of the catheter hub.

7. The retainer and medical device system as defined in claim 6, wherein the body of the retainer and medical device system further comprises one or more features configured to receive one or more portions of the medical device in a snap-fit arrangement.

8. The retainer and medical device system as defined in claim 1, wherein the body of the retainer and medical device system further defines a notch configured to receive therein a portion of a skin-placed dressing.

9. The retainer and medical device system as defined in claim 8, wherein the body of the retainer and medical device system defining the notch is configured to impart a compressive force on the skin-placed dressing when the portion of the skin-placed dressing is received in the notch.

10. The retainer and medical device system as defined in claim 8, wherein the skin-placed dressing is an antimicrobial disk.

11. The retainer and medical device system as defined in claim 10, wherein the first foot and the second foot each have a curved edge adjacent the nose portion to border an outer perimeter of the antimicrobial disk.

12. The retainer and medical device system as defined in claim 1, wherein the first foot includes a first living hinge adjacent the first base, and wherein the second foot includes a second living hinge adjacent the second base, the first living hinge and the second living hinge enabling movement of the first foot and the second foot with respect to the proximal arched portion, the central arched portion, and the nose portion.

13. A securement system, comprising:
the retainer and medical device system as defined in claim 1, and
at least one adhesive anchor pad configured to anchor the retainer and medical device system to a skin surface.

14. A securement and catheter assembly system, comprising:
a catheter assembly, comprising:
an external portion; and
an internal portion for insertion into a vasculature of a patient via a skin insertion site; and
a retainer comprising:
an arched portion extending from a first base to a second base to define a channel at a proximal end of the retainer, the first base and the second base defining a first plane, the channel engaging a hub of the catheter assembly extending along a first central axis extending parallel to the first plane;
a nose portion connected to the arched portion, the nose portion extending to a distal end of the retainer, the nose portion and the arched portion together providing a continuous outer surface from the proximal end of the retainer to the distal end of the retainer, the nose portion engaging one or both of a strain relief and a catheter tube of the catheter assembly extending along a second central axis angled relative to the first central axis, toward the skin insertion site; and
a first foot and a second foot each extending from the first base and the second base, respectively, on opposite sides of the arched portion, wherein a distal end of the first foot and a distal end of the second foot are proximal of the distal end of the retainer.

15. The securement and catheter assembly system as defined in claim 14, further comprising a first adhesive pad attached to the first foot and a second adhesive pad attached to the second foot.

16. The securement and catheter assembly system as defined in claim 14, wherein the catheter assembly is a peripheral IV catheter, and wherein the retainer is configured for placement on an arm of the patient to retain the peripheral IV catheter.

17. The securement and catheter assembly system as defined in claim 14, wherein the retainer includes one or more features configured to receive one or more portions of the catheter assembly in a snap-fit arrangement.

18. The securement and catheter assembly system as defined in claim 17, wherein the catheter assembly includes at least the strain relief, the one or more features includes a first pocket extending transversely from the channel in a first direction, and a second pocket extending transversely from the channel in a second direction, opposite of the first direction, wherein the first pocket and the second pocket are configured to receive a portion of the strain relief of the catheter assembly.

19. The securement and catheter assembly system as defined in claim 14, wherein the arched portion includes a lock window configured to receive an alignment ring of the catheter assembly.

20. The securement and catheter assembly system as defined in claim 14, wherein a notch is defined through the distal end of the retainer under the nose portion, wherein the notch is configured to receive therein a portion of a skin-placed dressing.

21. The securement and catheter assembly system as defined in claim 20, wherein the notch has a notch thickness less than a thickness of the skin-placed dressing to impart a compressive force on the skin-placed dressing when the portion of the skin-placed dressing is positioned in the notch.

22. The securement and catheter assembly system as defined in claim 20, wherein the skin-placed dressing is an antimicrobial disk.

23. The securement and catheter assembly system as defined in claim 22, further comprising at least one adhesive anchor pad shaped to border an outer perimeter of the antimicrobial disk when the portion of the antimicrobial disk is positioned in the notch.

24. The securement and catheter assembly system as defined in claim 14, wherein the first foot and the second foot both extend proximally of the arched portion.

25. A securement and catheter assembly system, comprising:
 a catheter assembly comprising:
  an external portion, including a hub and a strain relief and
  an internal portion for insertion into a vasculature of a patient via a skin insertion site; and
 a securement device, comprising:
  a body comprising:
   an arched portion at a proximal end of the body of the securement device, extending from a first base to a second base to define a first channel engaging the hub of the catheter assembly, the first base and the second base extending over a first plane, the hub extending along a first central axis parallel to the first plane;
   a nose connected to the arched portion, the nose extending to a distal end of the body of the securement device, the nose and the arched portion together providing a continuous outer surface from the proximal end of the body of the securement device to the distal end of the body of the securement device, a distal end of the nose defining a second channel engaging the strain relief of the catheter assembly, the strain relief extending along a second central axis at an angle relative the first central axis to deflect one or both of the strain relief and a catheter tube of the catheter assembly toward the skin insertion site;
   a first foot and a second foot extending laterally outward from the first base and the second base of the arched portion, each of the first foot and the second foot having a portion extending proximal of the arched portion, wherein a distal end of the first foot and a distal end of the second foot are proximal of the distal end of the body of the securement device; and
   a notch configured to enable a skin-placed dressing to be inserted through the distal end of the body of the securement device under the nose so that the skin-placed dressing is interposed between the body of the securement and a skin surface of the patient proximate the skin insertion site; and
  adhesive anchor pads permanently attached to the body of the securement and configured to attach the securement device to the skin surface of the patient.

26. The securement and catheter assembly system as defined in claim 25, wherein the first foot and the second foot extend arcuately and distally with respect to the arched portion, each including a living hinge configured to enable bending about the skin surface.

27. The securement and catheter assembly system as defined in claim 26, wherein the body of the securement device defining the notch is configured to impart a compressive force on the skin-placed dressing when a portion of the skin-placed dressing is received in the notch.

28. The securement and catheter assembly system as defined in claim 27, wherein the nose is configured to impart a portion of the compressive force on the skin-placed dressing.

29. The securement and catheter assembly system as defined in claim 28, wherein the body of the securement device includes a bottom opening communicating with one or both of the first channel and the second channel and configured to enable one or more of the hub, the strain relief, and the catheter tube of the catheter assembly to be received therein via a snap fit.

30. The securement and catheter assembly system as defined in claim 29, wherein the body of the securement device further includes a lock window configured to receive a lock tab included on the hub of the catheter assembly when the hub is received in the first channel.

31. The securement and catheter assembly system as defined in claim 30, wherein the lock tab is colored to provide a contrast to a surrounding structure of the catheter assembly.

32. The securement and catheter assembly system as defined in claim 31, wherein one of the first channel or the second channel of the body of the securement device includes a lock channel configured to receive an alignment ring of the hub of the catheter assembly, the alignment ring including the lock tab.

33. The securement and catheter assembly system as defined in claim 32, further comprising a comfort pad extending from one of the adhesive anchor pads and configured to be interposed between the catheter assembly and the skin surface of the patient.

34. The securement and catheter assembly system as defined in claim 33, wherein the first foot the second foot and the adhesive anchor pads are configured to enable the securement device to move in concert with the skin surface of the patient proximate the skin insertion site so as to prevent relative movement between the skin insertion site and the catheter tube of the catheter assembly extending through the skin insertion site when the securement device is attached to the skin surface with the catheter assembly received in the first channel and the second channel of the body of the securement device.

* * * * *